United States Patent
Boukhny

(10) Patent No.: US 6,852,093 B1
(45) Date of Patent: Feb. 8, 2005

(54) SURGICAL METHOD AND APPARATUS

(75) Inventor: Mikhail Boukhny, Laguna Niguel, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 10/842,106

(22) Filed: May 10, 2004

(51) Int. Cl.⁷ .................................. A61M 3/00
(52) U.S. Cl. .................................. 604/43
(58) Field of Search .................. 604/27, 28, 30, 604/35, 39, 43, 239, 264, 521, 289, 294, 297, 295, 301, 302; 433/80, 89

(56) References Cited

U.S. PATENT DOCUMENTS

| | | | | |
|---|---|---|---|---|
| 694,541 A | * | 3/1902 | Gordon | 604/39 |
| 2,458,876 A | * | 1/1949 | Rehn | 604/302 |
| 3,589,363 A | * | 6/1971 | Banko et al. | 604/22 |
| 3,994,297 A | * | 11/1976 | Kopf | 604/22 |
| 4,573,979 A | * | 3/1986 | Blake | 604/240 |
| 4,717,379 A | * | 1/1988 | Ekholmer | 604/43 |
| 4,904,238 A | * | 2/1990 | Williams | 604/43 |
| 5,123,902 A | * | 6/1992 | Muller et al. | 604/21 |
| 5,487,725 A | * | 1/1996 | Peyman | 604/22 |
| 5,616,120 A | * | 4/1997 | Andrew et al. | 604/28 |
| 5,674,226 A | * | 10/1997 | Doherty et al. | 606/107 |
| 5,902,292 A | * | 5/1999 | Feldman | 604/295 |
| 6,126,629 A | * | 10/2000 | Perkins | 604/22 |
| 6,485,452 B1 | * | 11/2002 | French et al. | 604/39 |
| 6,579,270 B2 | | 6/2003 | Sussman | |
| 6,695,821 B1 | * | 2/2004 | Sjaarda | 604/264 |
| 2003/0004455 A1 | | 1/2003 | Kadziauskas et al. | |
| 2003/0069594 A1 | | 4/2003 | Capetan et al. | |

* cited by examiner

*Primary Examiner*—Sharon Kennedy
(74) *Attorney, Agent, or Firm*—Jeffrey S. Schira

(57) ABSTRACT

A method and apparatus for directing relatively gentle pulses of heated surgical fluid against the capsular bag to assist in the removal of lens epithelial cells and cortical material adhered to the capsular bag.

2 Claims, 1 Drawing Sheet

SURGICAL METHOD AND APPARATUS

BACKGROUND OF THE INVENTION

This invention relates generally to the field of cataract surgery and more particularly to a method and apparatus for polishing the capsular bag following cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

Following lens removal, residual lens epithelial cells (LECs) and cortical material may remain adhered to the lens capsule. Removing this material has been increasingly recognized as being important in helping to prevent opacification of the posterior capsule (also known as a secondary cataract of PCO). PCO is generally treated by a second medical procedure known as a YAG capsulotomy during which a Nd:YAG laser is used vaporize a hole in the opacified posterior capsule to allow light to once again reach the retina. Currently, rubbing of the capsular bag with the tip of an irrigating/aspirating (I/A) handpiece is the technique used to "polish" the capsular bag. This mechanical debridement technique works well but is time consuming and risks tearing a hole in the capsular bag.

Therefore, a need continues to exist for a method and device for polishing the capsular bag following cataract extraction.

BRIEF SUMMARY OF THE INVENTION

The inventor of the present invention has discovered that the removal of LECs and cortical material from the capsular bag is enhanced by the use of a heated lavage technique. Such a technique may be practiced using commercially available surgical handpieces having a tip designed to direct relatively gentle pulses of heated surgical fluid against the capsular bag.

Accordingly, one objective of the present invention is to provide a method for the removal of LECs and cortical material adhered to the capsular bag.

Another objective of the present invention is to provide a handpiece that directs gentle pulses of heated surgical fluid against the capsular bag.

These and other advantages and objectives of the present invention will become apparent from the detailed description and claims that follow.

DETAILED DESCRIPTION OF THE INVENTION

Figure 1:
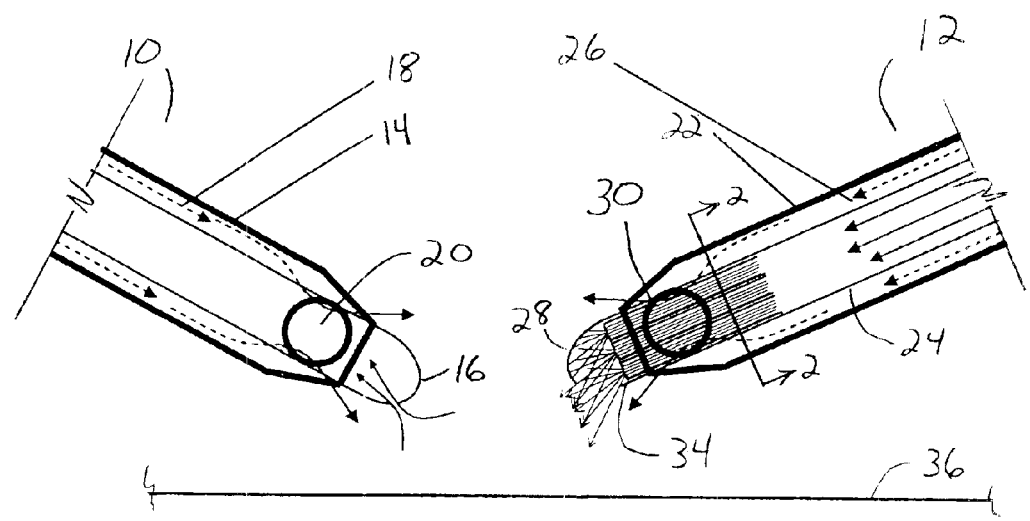
FIG. 1 is a partial cross-sectional view of the handpiece tips that may be used with the present invention.

As best seen in FIG. 1, the method of the present invention is generally practiced using I/A tip 10 and lavage tip 12 simultaneously in what is called a "Bi-Manual" surgical technique. I/A tip 10 may be any conventional I/A tip and generally includes outer silicone sleeve 14 and inner aspiration tube 16. Space 18 between sleeve 14 and tube 16 defines a pathway for irrigating solution to flow out port 20 and into the surgical site. Lavage tip 12 is of similar construction and generally contains a silicone sleeve 22 and inner tube 24 defining a first irrigating fluid path 26 that allows irrigating fluid to flow out of port 30. Inner tube contains a cover, shroud or hood 28 at distal end 34 that helps prevent fluid flowing out of inner tube 24 from striking directly, any object directly in front of tip 12.

Figure 2:
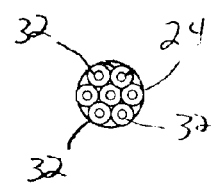
FIG. 2 is a cross-sectional view of the lavage tip of the present invention taken at line 2—2 in FIG. 1.

As best seen in FIG. 2, tube 24 contains a plurality of interior tubes 32, each occupying a portion of the interior diameter of tube 24. Interior tubes 32 separate the lavage fluid flowing down and out tube 24 into a plurality in individual jets or sprays. Such jets are directed against the inside of hood 28, thereby attenuating the velocity and force of the sprays exiting tubes 32 prior to contact with any tissue.

In use, I/A tip 10 is held in one hand by the surgeon and used in a conventional manner to aspirate tissue from the eye An irrigating fluid, such as a saline solution, simultaneously flows into the eye to help maintain the integrity of the eye and prevent anterior chamber collapse. Lavage tip 12 is held in the other hand by the surgeon and is connected to a suitable handpiece (not shown). One suitable handpiece is the AQUALASE® handpiece available commercially from by Alcon Laboratories, Inc., Worth, Tex. Lavage tip 12 is used to inject pulses of heated irrigating solution down tubes 24 and 32, against hood 28 and into the surgical site. The pressure, intensity or frequency of the fluid pulses may be any suitable amount, but generally will be less than those used to remove a cataractous lens because lavage tip 12 preferably is held near capsular bag 36 so that pulses of fluid exiting hood 28 strike capsular bag 36. Excessive pulse pressure could rupture capsular bag 36. Buy using hood 28 and reduced lavage pulse pressures, LECs and cortical materials may be removed more easily from capsular bag 36 without rupturing capsular bag 36. Ambient irrigating fluid is simultaneously injected down fluid path 26 and out port 30 along with the pulses of heated fluid. Such simultaneous fluid flow assists in lifted material off of capsular bag 36.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating cutting tips to enhance performance.

I claim:

1. A lavage tip for handpiece, comprising:
    a) an inner tube having a distal end coaxially mounted within an outer sleeve so as to form a fluid path between the inner tube and the outer sleeve;
    b) a plurality of interior tubes contained within the inner tube; and
    c) a hood at the distal end of the inner tube, the hood reducing the velocity of fluid exiting the interior tubes.

2. A method of polishing a capsular bag, comprising the steps of:
   a) holding a first handpiece tip near a capsular bag, the first handpiece tip having
      i) an inner tube having a distal end coaxially mounted within an outer sleeve so as to form a fluid path between the inner tube and the outer sleeve;
      ii) a plurality of interior tubes contained within the inner tube; and
      iii) a hood at the distal end of the inner tube, the hood reducing the velocity of fluid exiting the interior tubes;
   b) holding a second handpiece tip near the capsular bag, the second handpiece tip capable of aspirating tissue removed from the capsular bag; and
   c) directing fluid exiting the first handpiece tip against the capsular bag.

* * * * *